United States Patent [19]

Finch et al.

[11] Patent Number: 5,028,543

[45] Date of Patent: Jul. 2, 1991

[54] METHOD FOR MEASURING THE CONTENT OF HALOGENATED ORGANIC COMPOUNDS IN SOIL SAMPLES

[75] Inventors: Stephen R. Finch, Meriden, Conn.; David J. Fisher, North Adams, Mass.

[73] Assignee: Dexsil Corporation, Hamden, Conn.

[21] Appl. No.: 506,565

[22] Filed: Apr. 4, 1990

Related U.S. Application Data

[63] Continuation of Ser. No. 169,686, Mar. 18, 1988, abandoned.

[51] Int. Cl.$^5$ .............................................. G01N 33/26
[52] U.S. Cl. ...................................... 436/124; 436/60; 436/165; 436/140; 436/175; 422/61; 208/2; 210/909
[58] Field of Search ...................... 422/58, 61; 208/26, 208/2.1; 210/909; 436/175, 178, 179, 126, 165, 140, 60

[56] References Cited

U.S. PATENT DOCUMENTS

| | | | |
|---|---|---|---|
| 4,238,472 | 12/1980 | Albro et al. | 436/540 |
| 4,477,354 | 10/1984 | Fessler | 210/909 |
| 4,610,729 | 9/1986 | Keane | 210/639 |
| 4,662,948 | 5/1987 | Weitzman | 210/909 |
| 4,686,192 | 8/1988 | Fisher | 436/60 |

OTHER PUBLICATIONS

CLOR-N-OIL PCB Screening Kit Catalog, Dexsil Corp., Hamden, CT. 06517-3150, phone (203)-288-3509.

*Primary Examiner*—Robert J. Warden
*Assistant Examiner*—Lyle Alfandary Alexander
*Attorney, Agent, or Firm*—Victor E. Libert

[57] ABSTRACT

A method for measuring the halogenated organic compound content, e.g., polychlorinated biphenyl ("PCB") content, of soil samples may effectively be carried out with an inexpensive, disposable (that is, single-use) field test kit. The method includes contacting a weighted soil sample suspected of containing PCB or some other organohalogen contaminant with a pre-mixture of water and an organic solvent in which water is slightly soluble. The water extracts any inorganic halides which may be present and would adversely affect the accuracy of the test. The organic solvent wets the moist soil sample sufficiently to extract any PCB therein. The resultant organic solvent phase is separated from the soil sample and aqueous phase, dried by passage through a moisture-adsorbent material to remove or at least greatly reduce its moisture content, and analyzed by means of a color-change titration to determine halide content, and thereby the PCB (or other organohalogen) content, of the soil sample.

16 Claims, 2 Drawing Sheets

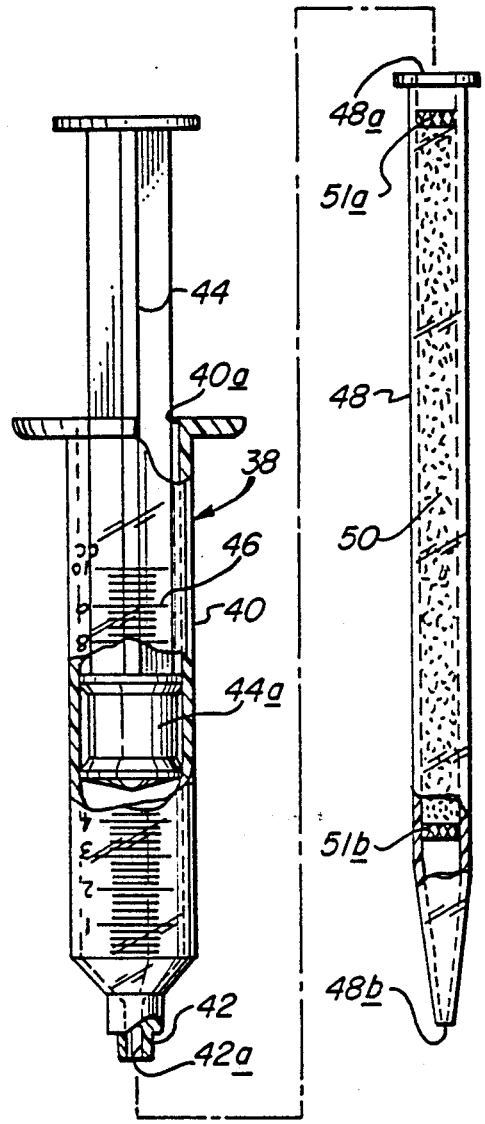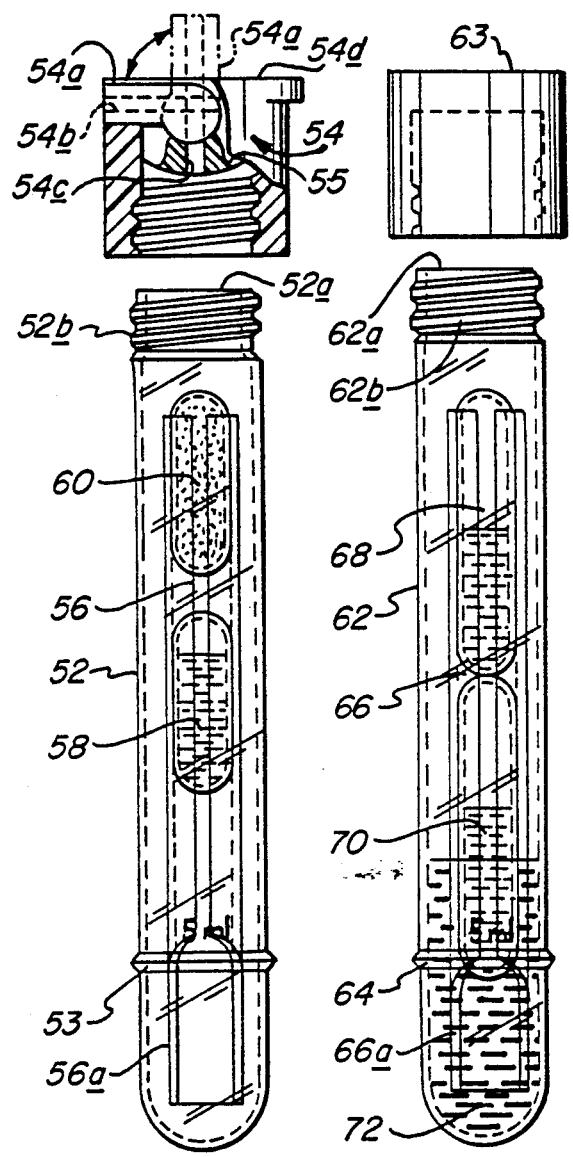
FIG. 1E    FIG. 1F    FIG. 1G    FIG. 1H

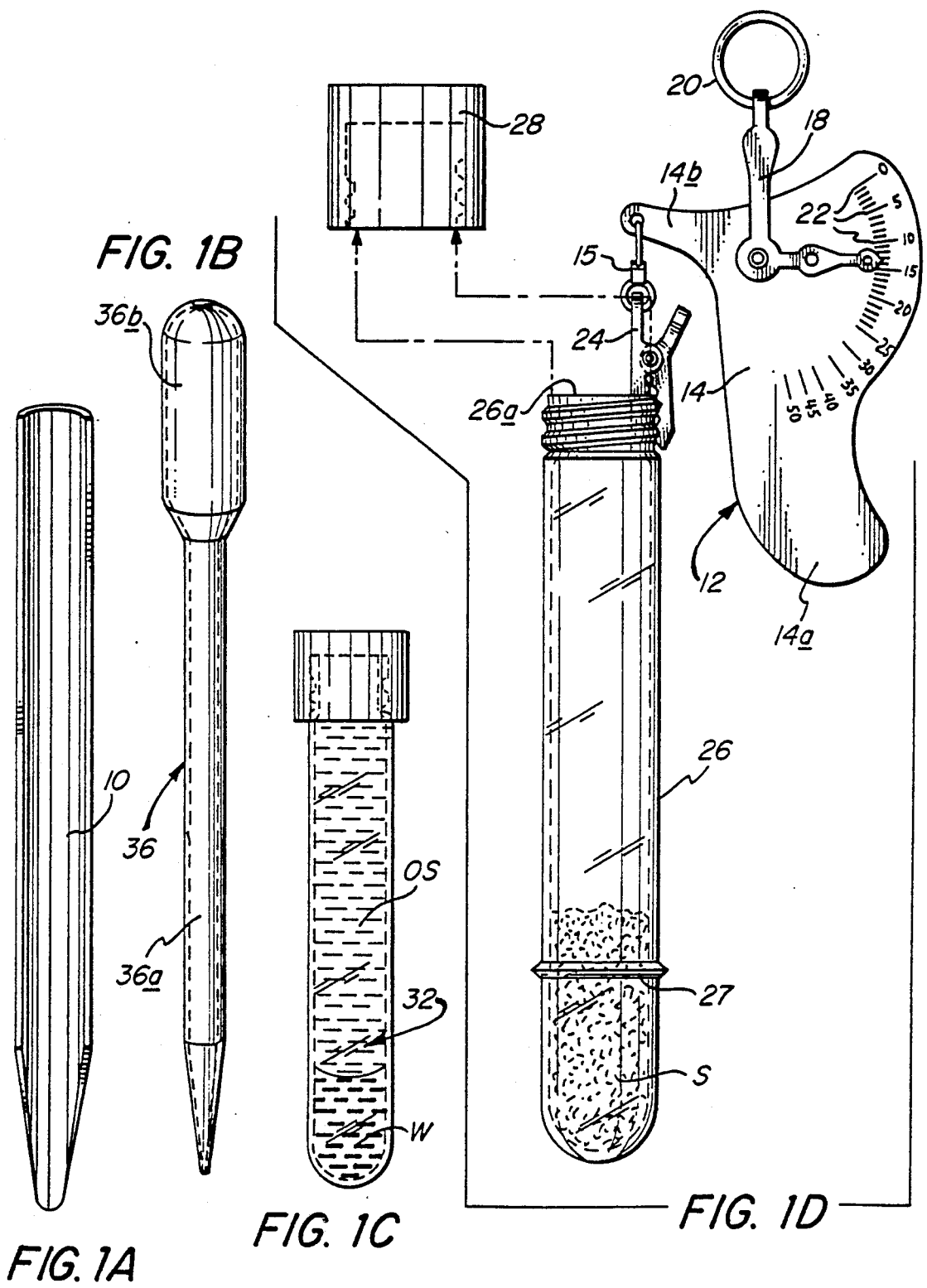

METHOD FOR MEASURING THE CONTENT OF HALOGENATED ORGANIC COMPOUNDS IN SOIL SAMPLES

This is a continuation of copending application Ser. No. 07/169,686 filed on Mar. 18, 1988, now abandoned.

BACKGROUND OF THE INVENTION

1. Field of the Invention

The present invention is concerned with a method for measuring the halogenated organic compound content of oils or other hydrocarbon liquids present as contaminants in soils. More particularly, the present invention is concerned with a method for using a test kit to make field analyses of the halogenated organic compound content of soil samples.

2. Description of Related Art

U.S. Pat. No. 4,686,192, issued on application Ser. No. 529,154 of David J. Fisher, discloses a chemical field test kit and method for detecting impurities in an oil sample. The oil sample is placed within the first of two test tube-shaped resilient containers in which are disposed breakable ampules containing reagents for the test. The ampules are broken within the resilient containers in a specified sequence by squeezing the container from the outside. The method of the Fisher Patent includes reacting the oil sample with an alkali metal and then adding an aqueous buffer/acid solution which is separated from the oil layer and transferred to a second container. A mercury titrant-containing ampule and then a dye indicator-containing ampule are broken within the second container, in order to indicate by a color change the level of halogen content of the oil sample.

Co-pending and commonly owned U.S. patent application Ser. No. 59,560, filed June 8, 1987 in the name of Theodore R. Lynn et al and entitled "APPARATUS AND METHOD FOR MEASURING HALOGEN CONTENT" discloses an apparatus, which may be embodied in a disposable field test kit, and a test method to measure the halogen content of hydrocarbon liquids. The apparatus includes a suction sampling means which provides close control of the quantity of sample taken. The pre-measured sample is solvated, then reacted with an alkali metal reagent which will form halides from the halogen material present, extracted into an aqueous phase, titrated and contacted with a color change indicator which acquires a characteristic color dependent upon the halogen content of the tested material.

PROBLEMS ENCOUNTERED IN THE FIELD OF THE INVENTION

Environmental protection laws and regulations of the Federal Environmental Protection Agency require that any waste oil containing more than a prescribed quantity of chlorine must be classified as a hazardous waste, and becomes subject to strict requirements concerning its disposal. Currently, the prescribed quantity is 1,000 parts by weight chlorine per million parts by weight of chlorine-containing oil. It is therefore necessary to determine the chlorine content of waste oils or other hydrocarbon liquids (below sometimes collectively referred to as hydrocarbon liquids) and to determine if they contain more or less than the specified level of chlorine which would constitute them as hazardous wastes. In cases where hydrocarbon liquids have permeated the ground, for example, as occurs in the case of oil spills, leaks from oil storage tanks, and the like, it becomes necessary to test the halogenated organic compound content of the hydrocarbon liquids permeating the soil. For obvious reasons of time and economy, it is desirable, at least during an initial survey of a given area, to be able to field test soil samples instead of having to return each sample to a laboratory for analysis. Further, the tests for the chlorinated hydrocarbon, e.g., polychlorinated biphenyl ("PCB"), content of soils is suitably carried out by a test which will detect halogenated organic compounds generally. However, as a practical matter, the testing is most often carried out to indicate the presence and quantity of PCB in the soil sample.

The testing of soil samples for PCB or other halogenated organic compound content presents a number of problems not encountered in testing oil or other liquid samples. These include the fact that almost all soils contain rather high concentrations of inorganic chlorides which must be eliminated from the test in order to avoid false high readings for chlorinated hydrocarbons. Further, it is extremely difficult to extract halogenated organic compounds such as PCB from soil samples, particularly if the soil samples contain a significant amount of moisture. Since the soil sample is washed with water as the most efficient way to extract inorganic halides from the sample, a wet soil sample results. Even in rare cases where washing to extract inorganic halides from the soil samples is not necessary, the soil often contains considerable natural moisture. The moist condition of the soil inhibits wetting of the soil by organic solvents which are substantially immiscible with water, apparently because the soil particles tend to have a film of moisture over them which shileds the soil particles from the water immiscible solvent. Thus, the use of substantially water-immiscible organic solvents such as benzene, hexane, etc., in attempts to wet moist soil samples sufficiently to adequately extract halogenated organic compounds from the soil sample proved unsuccessful. While this problem could be overcome by drying the soil samples as a preliminary step, pre-drying of the soil samples is not feasible if one desires a relatively inexpensive and lightweight field testing kit that is capable of giving on-the-spot results in the field.

SUMMARY OF THE INVENTION

In accordance with the present invention, there is provided a method for measuring the organic halide content of a soil sample. The method comprises the following steps. A quantity of soil is weighed to provide a soil sample of pre-determined weight. The weighed soil sample is contacted with a quantity of water to dissolve therein inorganic halides, if any, present in the soil sample and thereby provide an aqueous phase solution. A quantity of an organic solvent is provided, the organic solvent (1) being a solvent for halogenated organic compounds, and (2) being only partly miscible with water, so that water is sufficiently soluble in the organic solvent to enable the organic solvent to wet moist soil sufficiently to dissolve in the organic solvent halogenated organic compounds dispersed in the soil sample. The soil sample is contacted with the solvent to dissolve therein halogenated organic compounds, if any, contained in the soil sample and thereby provide an organic phase solution which is separated from the soil sample and the aqueous phase solution. The separated organic phase solution is then contacted with one or more reagents to provide a reaction residue, the quantity and type of reagents being selected to provide, in conjunction with the soil sample of pre-determined weight, a detectable indication of the organic halide content of the soil sample.

In one aspect of the present invention, the steps of contacting the soil sample with the water and contacting the soil sample with the organic solvent are carried out simultaneously, by contacting the soil sample with a mixture of the water and the organic solvent, e.g., by shaking a container containing the soil sample and a mixture of water and the organic solvent. In such case, the organic solvent is one in which water has sufficient solubility to enable the organic solvent to wet soil which is dispersed in a mixed organic solvent/aqueous phase sufficiently to dissolve in the organic solvent halogenated organic compounds, e.g., PCB, dispersed in the soil sample.

In another aspect of the present invention, the organic phase solution is dried before the step of contacting it with the reagent(s), e.g., by passing it through a bed of water-adsorbent material such as magnesia alumina silicate.

In another aspect of the present invention, the mixture of water and the organic solvent contains from about one (1) to two (2) parts by weight of water and from about four (4) to twenty (20) parts by weight of the organic solvent.

In yet another aspect of the present invention, the organic solvent is one in which water has a solubility of at least about 1 gram of water per 100 grams of solvent, preferably from about 1 to 5, more preferably from about 1 to 2, grams of water per 100 grams of solvent at 25° C.

A preferred class of solvents is one or more unhalogenated, unhydroxylated diethers; a preferred solvent comprises diethylene glycol dibutyl ether.

Reference in the specification and/or the claims to the "organic chloride" or "organic halide" content of the soil sample, unless the context clearly requires otherwise, means the soil sample's chloride or halide content which originated from chlorinated or halogenated organic compounds in the sample, e.g., from halogenated hydrocarbons such as PCB.

Other aspects of the invention, including the utilization of other specific solvents and classes of solvents and specific analytical reagents and classes of reagents, will be apparent from the following description.

BRIEF DESCRIPTION OF THE DRAWINGS

FIGS. 1A–1H show in elevation the components of a field test kit useful for carrying out an embodiment of the present invention.

DETAILED DESCRIPTION OF THE INVENTION AND PREFERRED EMBODIMENTS THEREOF

The method of the present invention includes taking a weighed soil sample and contacting it with both water and a selected organic solvent for halogenated organic compounds, which solvent is one which is only partly miscible with water so that water is only slightly soluble in the organic solvent. Inorganic halides, such as salt (sodium chloride) which may be contained in the soil sample are dissolved in the aqueous phase and halogenated organic compounds, such as PCB, which may be contained in the soil sample are dissolved in the organic phase.

The slight miscibility, i.e., slight solubility of water in the organic solvent is believed to enable the solvent to wet moist soil particles sufficiently to adequately extract from the soil sample halogenated organic compounds, if any, present in it. Without wishing to be bound by any particular theory, it is believed that the slight solubility of water in the organic solvent enables the organic solvent to penetrate the film of moisture which surrounds particles of moist soil. The film of moisture acts as a shield against contact of the moist soil particles by organic solvents which are substantially immiscible with water, i.e., in which water is substantially insoluble. The organic solvent should not be one with which water is totally miscible because the organic solvent is ultimately to be separated from the aqueous phase mixed with it, as explained below. By separating the organic solvent from the aqueous phase and the inorganic halides dissolved therein, the latter are not recorded as false positives in a subsequent test for the organic halide content of the organic solvent.

In one technique in accordance with the present invention, the soil sample may be separated from the water phase containing the extracted inorganic halides before being contacted with the organic solvent. For example, after adding water to the soil sample and shaking it to promote good contact between the soil sample and the water to extract inorganic halides, if any, from the soil sample into the water, the water may be decanted, preferably through a sieve in order not to lose soil particles. However, this technique requires additional manipulation, e.g., back-washing the sieve to recover any soil sample retained on it, and may well result in a loss of some of the soil sample, thereby reducing the accuracy of the test.

Accordingly, it is a preferred technique in accordance with the present invention to extract the inorganic halides with water and to extract the halogenated organic compounds with an organic solvent, without first separating the aqueous phase from the soil sample. Thus, in a preferred embodiment of the invention, the water and organic solvent are both added to the soil sample, the mixture is shaken to promote good contact between the liquid (comprising aqueous and organic solvent phases) and the soil sample, and the organic phase is then separated from the residual soil sample and the aqueous phase. The separated organic phase may then be dried and tested by any suitable method to determine its organic halide content. For example, a wet chemistry titration method is conveniently used to determine the organic halide content of the dried organic phase, thereby establishing the halogenated organic compound content of the soil sample. With this simultaneous water/organic solvent contacting technique, and in accordance with a preferred embodiment of the invention, the water and the organic solvent may be pre-mixed in desired proportion, and the resultant pre-mixture of water and organic solvent added to the soil sample.

Although the method of the invention has broad applicability, one of its significant advantages is that it may be accurately carried out in a field test kit and moreover, in a field test kit which is sufficiently inexpensive that it is economically feasible to use the kit once and then discard it. A suitable field test kit for carrying out the method of the invention conveniently employs pre-packaged reagents in accurately measured quantities thereby facilitating the use of the test kit by inexperienced personnel with very little or no prior training.

The drawings illustrate the contents of a typical field test kit, which may be conveniently packaged, for example, in a small cardboard container (not shown in the drawings). Instructions (not shown) for using the kit may also be included in the kit, including a color chart to illustrate a color-change titration. The container may be formed with an extension flap which is folded and fastened into a box channel in which spaced-apart circular perforations are formed. The box channel thus formed is stiff enough to act as a test tube rack for the test tubes forming part of the apparatus, thereby facilitating use of the kit in the field.

Referring now to the drawings, FIG. 1A shows a scoop 10, which may be made of steel, for digging and removing soil samples from the ground. Scoop 10 is conveniently made U-shaped in cross section, both to enhance its mechanical strength for digging and to facilitate pouring of the resultant soil sample into test tube 26 (FIG. 1D) as described below. Test tube 26 is fitted with a removable screw-on cap 28 and has a volume indicia 27, five milliliters in the illustrated case, inscribed thereon. FIG. 1D shows a conventional, small, handheld scale 12 comprising a flat body 14 having a pointer 16 and a beam 18 pivotably mounted thereon. Pointer 16 and balance beam 18 comprise a generally L-shaped unitary member having a ring 20 carried at the free end of balance beam 18. A weight scale 22, which may be calibrated in grams and/or ounces, is suitably printed or inscribed upon body 14 which includes a counterweight extension 14a. A spring-loaded alligator-type mounting clip 24 is secured by chain 15 to body 14 at arm 14b thereof. Mounting clip 24 is used to hold first test tube 26 (FIG. 1D) for weighing a soil sample S placed therein by means of scoop 10, while ring 20 is held between the operator's thumb and forefinger.

FIG. 1B shows a squeeze-bulb syringe or pipette 36, comprising a stem 36a and a squeeze bulb 36b. Both stem 36a and bulb 36b may be inexpensively made of molded synthetic organic polymeric material, e.g., polyethylene.

FIG. 1C shows a glass test tube 32 having a removable screw-on cap 34 thereon and containing 10 milliliters of a suitable organic solvent OS, e.g., diethylene glycol dibutyl ether (also known as butyl digylme), and two milliliters of water W.

FIG. 1E shows a conventional hypodermic syringe 38 comprising a hollow, barrel-shaped body 40 having an open end 40a through which is inserted the usual plunger 44 on which is mounted a piston 44a. The opposite end of body 40 carries a protruding discharge outlet 42 of generally cylindrical or truncated-cone configuration having a discharge passage 42a. The exterior of syringe 38 carries volume indicia 46. A syringe having a 10 milliliter volume capacity as illustrated is suitable for purposes of carrying out a field test embodiment of the method of the present invention.

FIG. 1F is a tube or funnel 48 having an inlet end 48a and an outlet end 48b which is of smaller diameter than inlet end 48a. Funnel 48 contains a bed 50 of suitable water adsorbent and/or absorbent material such as, for example, 4 grams of particles of 100 to 120 mesh size of a magnesia alumina silicate. A magnesia alumina silicate absorbent is commercially available under the trademark "FLORISIL" and is suitable for purposes of the invention. Funnel 48 may also be made of a plastic material such as polyethylene. Retaining screens 51a and 51b are positioned, respectively, at the top and bottom of bed 50, i.e., respectively adjacent inlet end 48a and outlet end 48b of funnel 48, in order to retain particles of the adsorbent material within funnel 48. The screens 51a, 51b may conveniently be made of a polypropylene felt material or any suitable material which is porous to the organic phase solvent. In order to protect water-adsorbent bed 50 from the atmosphere during storage, funnel 48 may have air and moisture-tight removable caps (not shown) at inlet and outlet ends 48a, 48b, or it may be packaged in a sealed air-tight and moisture-proof container, such as a foil envelope (not shown).

FIG. 1G shows a test tube 52 having a mouth 52a and screw threads 52b thereon. A volume indicia 53 is provided on tube 52 and, in the illustrated embodiment, shows a 5 milliliter volume. A removable plastic dispenser cap 54 is screw-mounted on test tube 52 and includes a pivotable spigot 54a mounted on cap 54 for pivoting movement between a closed position and an open position. The closed position is illustrated in solid line rendition in FIG. 1G, in which a spigot conduit 54b, which extends through spigot 54a, is isolated from a cap conduit 54c which extends through a hemispherical base portion 55 of cap 54. Cap 54 has a flat top 54d and is configured so that spigot 54a is flush with, or below, flat surface 54d when spigot 54a is in the closed position shown in solid line in FIG. 1G.

Test tube 52 contains an ampule support 56 comprising a longitudinally split and shaped tube of stiff but flexible plastic material within which a first glass ampule 58 and a second glass ampule 60 are contained. Ampules 58 and 60 have an outside diameter somewhat greater than the inside diameter of the tube from which ampule support 56 is fashioned, so that the elastic resiliency of ampule support 56 causes the split tube to firmly grip the first and second ampules therewithin. Ampule support 56 is supported by a leg portion 56a thereof which is seated at the bottom end of test tube 52. First ampule 58 contains a solution of butyl diglyme and naphthalene. Second ampule 60 contains an alkali metal reactant, such as a dispersion of fine particles of sodium metal in a suitable vehicle such as a light, clear, unhalogenated mineral oil.

FIG. 1H shows a test tube 62 having a mouth 62a, screw threads 62b and a screw-on cap 63. Test tube 62 may be identical to test tubes 26 and 60, including the inclusion of a volume indicia 64 showing, in the illustrated embodiment, a 5 milliliter volume line. An ampule support 66 is identical in construction to ampule support 56, and includes a leg portion 66a at the bottom thereof. Support 66 carries within test tube 62 a third glass ampule 68 containing a mercuric nitrate solution and a fourth glass ampule 70 containing a solution of s-diphenyl carbazone. Test tube 62 also contains an aqueous buffer solution therein, e.g., 7 ml of an aqueous buffer solution 72.

Test tubes 26 (FIG. 1D), 52 (FIG. 1G) and 62 (FIG. 1H) may be identical to each other for the sake of standardization even though, for example, the volume indicia 27 is not needed on test tube 26. Each of test tubes 26, 52 and 62 is made of a plastic, such as polyethylene, and is designed to be sufficiently resilient and flexible for purposes to be described below. Caps 28, 54 and 63 may be made of contrasting colors to facilatate identifying specific tubes in the kit instructions.

The components illustrated in FIGS. 1A through 1H inclusively, comprise the contents of a field kit suitable for use in practicing the invention, and may be packaged in any suitable container or containers (not shown) together with instructions for carrying out the test.

Although the method of the invention is, as noted above, broadly applicable to testing for halogenated organic compounds generally, for economy of expression the following description of the use of the illustrated test kit will refer to PCB testing, the most common use contemplated for the kit, and will refer to specific reagents and specific reagent and soil sample quantities actually utilized in a field test kit commercially available from Dexsil Corporation, the assignee of this application.

The plastic test tube 26 is, as illustrated in FIG. 1D, fastened to scale 12 by having mounting clip 24 secured to the rim of the mouth 26a of test tube 26. Scoop 10 is used to procure a soil sample from an area which is suspected of being contaminated with a halogenated organic compound and, with the operator holding scale 12 by means of ring 20, sufficient soil S is added to test tube 26 until the scale shows that the desired weight of soil has been added. For example, sufficient soil S is added to a test tube 26 weighing 6 grams to register a weight of 16 grams on the scale, indicating that a total of 10 grams of soil sample S has been placed in the tube 26. The scale 12 is then removed from test tube 26. Cap 34 is then removed from glass test tube 32 and its entire contents, comprising the organic solvent OS and water W, are poured into plastic test tube 26, after which cap 28 is replaced on test tube 26 and securely tightened. Any clumps of soil in sample S may be broken by squeezing the flexible sides of test tube 26, and the tube 26 is then vigorously shaken for one minute. The contents of the tube are then allowed to settle for two minutes, or until the soil is well compacted at the bottom of the tube 26, with the organic solvent phase on top, above the soil and the aqueous phase. Settling of the soil can be facilitated by gently tapping the bottom of the tube on the ground or any hard surface. The test tube 26 can be supported by any suitable means, preferably the test tube rack (not shown) built into the kit container as described above, so that the tube is held still while the soil settles.

While the soil sample S is settling, test tube 52 is placed in an upright position, which may be conveniently carried out by fitting it into the container test tube rack (not shown), and cap 54 is removed from test tube 52 and plunger 44 is removed from syringe 38. Plastic funnel 48 is then removed from its protective wrapping (not shown), such as a sealed foil envelope, which protects the bed 50 of adsorbent material from air. (Adsorbent material such as magnesia alumina silicate absorbs moisture from air, and so funnel 48 is not removed from its protective wrapping until it is needed for use.) The discharge outlet 42 of syringe body 40 is promptly fitted into inlet end 48a of funnel 48. Discharge outlet 42 and inlet end 48a are each dimensioned and configured so that discharge outlet 42 forms a snug, sealing fit when forced into inlet end 48a of funnel 48. The connection is indicated schematically by the dot-dash line connecting syringe 38 (FIG. 1E) and funnel 48 (FIG. 1F).

The funnel 48 is then partially inserted into test tube 52 and pipette 36 is used to remove organic phase solvent from test tube 26, picking up as little as possible of the aqueous phase and soil sample. Any soil sample and aqueous phase picked up will be adsorbed in and/or filtered from the organic phase solution by bed 50 of adsorbent, but care should be taken to impose as small a demand as possible on the capacity of adsorbent bed 50 by taking up into syringe 36 as little of the soil and aqueous phase as possible. The organic solvent phase thus removed is dispensed into body 40 of syringe 38 through the open end 40a thereof, plunger 44 having previously been removed from syringe 38.

After the organic solvent has been placed within syringe 38, plunger 44 is replaced within body 40 through open end 40a and the plunger is then utilized to force the solvent from syringe 38 through funnel 48 and the adsorbent bed 50 contained therein. Enough pressure is applied to plunger 44 so that about two or three drops of solvent per second are discharged through outlet end 48b of funnel 48 to insure adsorption of substantially all the moisture from the organic phase, as well as the filtration of any soil particles therefrom. As mentioned above, one reason for drying the organic phase solvent is to remove with removed residual water any inorganic halides dissolved in the water, as such inorganic halides would adversely affect the accuracy of the test for the presence of organic halides in the organic solvent. It should be noted that if some small amount of inorganic halide does remain in the dried organic phase solvent, the test results will be shifted in a positive direction, i.e., will show higher than actual halide content, thus providing a safety factor. That is, a false positive result (one showing a higher than actual organic halide content) will lead to precautions and/or further testing and will not result in the false security which follows from a false negative test result (a reading lower than the actual organic halide content.) Another reason for drying the organic phase solvent is that a preferred quantitative test for halogenated organic compounds includes reaction with an alkali metal reagent (as described below) and this reaction is hindered by the presence of water. Thus, drying of the organic phase solvent may be useful or necessary as a preliminary step for contacting it with one or more reagents to provide a detectable indication of the organic halide content of the soil sample.

When the dried solvent reaches the 5 milliliter indicia line 53 on test tube 52, the plunger 44 is pulled back to stop the flow of solvent through funnel 48, which is then removed from test tube 52. Syringe 38 and funnel 48 may be discarded at this point, along with test tube 26. Dispenser cap 54 is then replaced on test tube 52 and screwed tightly into place with its pivotable spigot 54a in the closed position shown in solid line in FIG. 1G. Plastic test tube 56 is sufficiently resilient so that by squeezing it from the outside, glass first ampule 58, which contains butyl diglyme and naphthalene, is crushed or broken to release its contents, after which the tube is shaken for about 10 seconds to mix the contents of ampule 58 with the 5 milliliters of organic phase solvent. Glass second ampule 60, which contains the alkali metal reactant, e.g., sodium metal, is then similarly crushed or broken to release its contents, which are allowed to react for about 60 seconds, with intermittent shaking several times during the one-minute reaction period. The metallic sodium (or other alkali metal reagent) will react with halogen materials in the dried organic phase solvent, such as with PCB (and/or other chlorinated hydrocarbon compounds present) to form sodium halides, e.g., sodium chloride. In this manner, organic chloride (or halide) compounds contained in the organic phase solvent are converted to an equivalent quantity of inorganic chloride (or halide) compounds, e.g., sodium chloride. The alkali metal reactant may be provided as the elemental alkali metal or as one or more suitable organometallic compounds of alkali metals. For example, metallic sodium or lithium may be used, or sodium biphenyl or sodium naphthalene.

At this stage of the test procedure, cap 54 is unscrewed from test tube 52 and cap 63 is unscrewed from test tube 62 which contains the extractant liquid 72. Extractant liquid 72 is poured from test tube 62 into test tube 52 and cap 54 is then screwed tightly into place on test tube 52, with spigot 54a in the closed position shown in solid line in FIG. 1G. Test tube 52 is then shaken vigorously for about 10 seconds and vented by partially unscrewing cap 54. Cap 54 is then re-tightened and test tube 52 is again shaken vigorously for an additional period of time, say 10 seconds. The venting is repeated and cap 54 is again re-tightened, after which test tube 52 is positioned upside down (with mouth 52a at the bottom) by placing the flat surface 54d of cap 54 on any convenient flat surface. Test tube 52 is then left undisturbed for at least about two minutes in order to allow the separation of an aqueous phase and the organic solvent phase.

The extractant liquid 72 may comprise an aqueous solution containing sodium sulfate, sulfuric acid, monosodium phosphate and cadmium sulfate. The sodium sulfate serves as an emulsion breaker so that if the soil sample tested should contain a high concentrations of surfactants, the tendency of the surfactants to form emulsions is overcome and a clean separation of the admixed organic phase solvent and extractant liquid into respective aqueous and organic solvent phases is obtained. The sulfuric acid content of the liquid extractant is sufficient to neutralize any unreacted metallic sodium and, in combination with the monosodium phosphate, provide a sodium acid phosphate buffer to maintain a pH level appropriate for carrying out the analytical determination. The cadmium sulfate serves to react with any sulfur compounds, e.g., bisulfides and sulfides, which may be present in the test soil sample and, if unreacted, might interfere with the analytical determination.

After the organic and aqueous phases are fully separated by the organic phase rising to the top of the liquid within test tube 52, leaving the aqueous phase below it and in contact with cap 54, test tube 52 is gently picked up while being maintained in an upside down position with cap 54 pointed downwardly, and positioned above the opening provided by mouth 62a of test tube 62. Pivotable spigot 54 is then moved to its open position (illustrated in dash lines in FIG. 1G) and the sides of test tube 52 are gently squeezed to dispense through conduit 54b of spigot 54a, and into test tube 62, a quantity of the separated aqueous phase sufficient to fill tube 62 up to the 5 milliliter indicia line 64 thereon. With this precisely measured (by indicia 64) 5 milliliter quantity of the aqueous phase material thus placed within test tube 62, cap 63 is screwed tightly thereon to seal it. Third ampule 70, which contains a pre-measured quantity of a mercuric nitrate titrant, is then crushed to release its contents within test tube 62 by pinching the tube from the outside in the manner as described above. Tube 62 is then vigorously shaken for about 10 seconds to thoroughly mix the reactants.

Fourth ampule 68, which contains a color change indicator such as diphenyl carbazone or a combination of diphenyl carbazone and bromphenyl blue, is then similarly crushed from the exterior of test tube 62 by pinching the latter, to release the indicator, and the contents are shaken for an additional 10 seconds. A distinctive color or color change is provided by the indicator material depending on whether or not the amount of halide, e.g., chloride, present was greater or less than the equivalent amount of titrant. For example, inorganic chlorides formed by reaction of the alkali metal reagent with the chlorine material content of the sample react with the mercuric nitrate titant to form mercuric chloride. If the amount of chloride ions in the aqueous phase is insufficient to consume all the mercuric ions, excess mercuric ions react with the diphenyl carbazone dye indicator to provide a characteristic blue or blue-violet color. On the other hand, if the amount of chloride ions is sufficient to react with all the mercuric ions, the reaction residue remains colorless or has a yellowish cast. Thus, by pre-selecting the amount of titrant and the soil sample size, the color change point may be selected at any desired level of chlorine (or other halogen) material content of the sample to be tested.

The test procedure as described above is a specific case of providing a detectable indication of the organic halide content of the organic phase solvent, and thus of the soil sample, by drying the organic phase solution which has been separated from the soil sample and the aqueous phase solution, and treating the dried organic phase solution as follows: contacting the dried organic phase solution with an alkali metal reagent to react the latter with any halogenated organic compounds in the organic phase solution to form alkali metal halides therefrom; contacting the resultant reacted organic phase solution with an aqueous extractant to extract the alkali metal halides from the organic phase into an aqueous extractant phase, and separating the aqueous extractant phase from the organic phase solution; titrating the alkali metal halides in the aqueous extractant phase with a pre-measured quantity of a titrant; and then contacting the titrated aqueous extractant phase with an indicator which acquires a characteristic color depending upon whether or not the quantity of alkali metal halides present in the aqueous extractant phase is sufficient to react with all of the added titrant, whereby the resultant color provides the detectable indication of whether or not a pre-selected level of halogen was present in the soil sample.

The foregoing discussion applies equally to bromine and iodine materials, although it will be appreciated that chlorinated organic compounds, particularly chlorinated hydrocarbons, are of primary environmental concern. For example, the present invention enables accurate field detection of threshold levels of PCB and other organochloride compounds in the soil, such as occurs when PCB or materials containing it, e.g., hydrocarbon liquids containing PCB, are spilled. The pre-encapsulated reagent quantities are carefully controlled, and the test kit permits the taking of a reasonably precisely weighed quantity of soil sample so that, as confirmed by the data reported below, reliable test results are obtained.

EXAMPLE I

The commercially available field test kit includes components substantially as shown in the drawings and described above, including a moisture- and air-tight envelope within which funnel 48 is packaged. The field test kit also includes test tubes corresponding to test tubes 56 and 62 of the drawings, which contain ampules fitted as follows:

| Item (FIG.) | Component |
|---|---|
| 58 (FIG. 1G) | Breakable glass ampule containing 250 microliters of a solvent comprised of 75% by weight of diethylene glycol dimethyl ether and 25% by weight of naphthalene. |
| 60 (FIG. 1G) | Breakable glass ampule containing 70 mg of metallic sodium dispersed in halogen-free mineral oil. |
| 68 (FIG. 1H) | Breakable glass ampule containing 0.75 ml of a standard mercuric nitrate aqueous solution. |
| 70 (FIG. 1H) | Breakable glass ampule containing 0.5 ml of diphenylcarbazone indicator in ethyl alcohol. |
| 72 (FIG. 1H) | 7 ml of aqueous extractant liquid comprising an 8% solution of sodium sulfate, containing buffering agents to provide an analytical buffer, and 0.0112 g of cadmium sulfate. |

The method of the present invention, which is conveniently carried out in the field by use of a single-use test kit in accordance with Example 1, results in substantially only organic halides (if any were present in the soil sample) being dissolved in the organic phase solvent, because all or most of the inorganic halides (if any were present in the soil sample) were separated from the organic solvent with the water phase. The reagent quantities and prescribed sample size for the field test kits were selected to provide a color change at 20 parts per million by weight ("ppm") of (organic) halide in the soil samples. If the particular halogenated organic compound or compounds present in the soil sample are known or determined, the ppm of organic halide determined by the test can be used to calculate the ppm of halogenated organic compounds in the soil sample. Thus, an organic chloride level of 20 ppm is approximately equivalent to 50 ppm PCB in the soil sample.

EXAMPLE 2

In field tests, a number of the commercially available test kits of the type shown in FIGS. 1A–1H and described in Example 1 above, were sent to a number of different users for use in testing soil samples under a variety of conditions. Duplicate soil samples were taken in each case so that samples identical to those tested in the field kits could also be tested in laboratory conditions utilizing a modification of an ASTM procedure. ASTM Method D 808-63 (81), *Chlorine in New and Used Petroleum Products (Bomb Method)*, was modified by replacing the gravimetric finish with a potentiometric titration technique as reported by a Research Triangle Institute (RTI) study for the Federal Environmental Protection Agency (EPA). This EPA study is reported in A. Gaskill, Jr., and E. D. Estes, *Development and Validation of Sample Preparation and Analysis Procedures for Determination of Inorganic and Organic Chlorine and Other Halogen Species in Used and Waste Oils*, Final Report, EPA Contract No. 68-01-7075, Work Assignment No. 18, U.S. EPA, Office of Solid Waste, November 1985. ASTM Method D 808-63 (81) and the EPA study are incorporated by reference herein.

Seventy-five tests were conducted utilizing the field test kits to carry out the described embodiment of the present invention, and seventy-five duplicate soil samples were tested by the laboratory method. Of the seventy-five tests conducted with the field test kits, 47 true negatives were reported. That is, 47 of the samples tested by the field test kits showed less than 50 parts per million by weight of PCB (or other organohalogen) and these findings were confirmed by the gas chromatography laboratory tests on the corresponding duplicate samples. The field test kits also recorded 20 true positive readings, i.e., in 20 cases the results of the test kit indicated more than 50 parts per million of halogenated organic compounds in the soil and the laboratory gas chromatography tests on the duplicate samples confirmed these findings. In only 8 cases the field test kit of the invention gave false positive results, i.e., the field test kit showed more than 50 parts per million of halogenated organic compounds in the soil, whereas for the corresponding duplicate samples, the gas chromatography laboratory test showed less than 50 parts per million halogen.

It is significant, as shown by the results of Example 2, that no false negatives were provided by the field test kits, that is, in no case did the field test kit report less than 50 parts per million when the laboratory gas chromatography showed a higher reading. Thus, the few errant results of the disposable field test kits were on the safe, conservative side, giving false positive readings which were later negated by the much more expensive laboratory tests. This shows that the field test kit provides a safe and reliable test method for identifying PCB (or other halogenated organic compound) contamination of the soil. Accordingly, the field test kit may be used to preliminarily screen in the field of a large number of samples by relatively untrained personnel using inexpensive, disposable kits. The preliminary screening serves to identify uncontaminated and at least potentially contaminated areas, so that the much more expensive laboratory resources may be conserved for testing only those samples taken from areas indicated to be positive by the field test kit.

While the invention has been described in detail with respect to specific preferred embodiments thereof, it will be apparent, upon a reading and understanding of the foregoing, that variations thereto may occur to those skilled in the art and it is intended to include such variations within the scope of the appended claims. For example, actual levels of halogen in the soil sample can be determined by using the reagents and apparatus of the illustrated field test kit by modifying the kit and instructions to carry out color change endpoint titrations instead of the fixed point titration provided by the pre-measured kit reagents. The method of the invention of course could also be utilized by means other than the illustrated test kit, e.g., it could be carried out in a laboratory using conventional laboratory apparatus. Similarly, any suitable titration or other quanitative analysis could be used to determine the organic halide content, or whether or not a specified organic halide content threshold is exceeded, of the organic phase solution, and thereby of the soil sample.

What is claimed is:

1. A method for measuring the organic halide content of a soil sample, the method comprising:
   (a) weighing a quantity of soil to provide a soil sample of pre-determined weight;
   (b) contacting the soil sample with a quantity of water at least sufficient to dissolve therein inorganic halides, if any, present in the soil sample and thereby provide an aqueous phase solution and render the soil sample moist;

(c) contacting the soil sample with a quantity of an organic solvent at least sufficient to dissolve therein halogenated organic compounds, if any, contained in the soil sample and thereby provide an organic phase solution, the organic solvent (1) being a solvent for halogenated organic compounds, and (2) being only partly miscible with water, so that water is sufficiently soluble in the organic solvent to enable the organic solvent to wet moist soil sufficiently to dissolve in the organic solvent halogenated organic compounds, if any, which were dispersed in the soil sample;

(d) separating the resultant organic phase solution from the soil sample and the aqueous phase solution; and (e) contacting the separated organic phase solution with one or more reagents to provide a reaction residue, the quantity and type of reagents being selected to provide, in conjunction with the soil sample of pre-determined weight, a detectable indication of the organic halide content of the soil sample.

2. The method of claim 1 wherein the organic solvent is one in which water has sufficient solubility to enable the organic solvent to wet soil which is dispersed in a mixed organic solvent/aqueous phase sufficiently to dissolve in the organic solvent halogenated organic compounds dispersed in the soil sample, and including carrying out steps (b) and (c) simultaneously by contacting the soil sample with a mixture of water and the organic solvent.

3. The method of claim 2 wherein the mixture of water and the organic solvent contains from about 1 to 2 parts by weight of water and from about 4 to 20 parts by weight of the organic solvent.

4. The method of claim 1, claim 2 or claim 3 including drying the organic phase solution of step (d) prior to step (e).

5. The method of claim 4 including drying the organic phase solution by passing it through a bed of moisture-adsorbent material.

6. The method of claim 1, claim 2 or claim 3 wherein the organic solvent comprises one or more unhalogenated, unhydroxylated diethers.

7. The method of claim 1, claim 2 or claim 3 wherein the organic solvent is selected from the class consisting of butyl ether, butyl diglycol dimethyl ether, n-amylether, isoamylether, diethylene glycol dimethyl ether, diethylene glycol diethyl ether, diethylene glycol dibutyl ether and mixtures of two or more thereof.

8. The method of claim 1, claim 2 or claim 3 wherein the organic solvent comprises diethylene glycol dibutyl ether.

9. The method of claim 1, claim 2 or claim 3 wherein the organic solvent is one in which water has a solubility at 25° C. of from about 1 to 2 grams of water per 100 grams of solvent.

10. The method of claim 1, claim 2 or claim 3 including drying the organic phase solution of step (d) prior to step (e), and wherein step (e) is carried out by contacting the dried organic phase solution with an alkali metal reagent to react the latter with any halogenated organic compounds in the organic phase solution to form alkali metal halides therefrom; contacting the resultant reacted organic phase solution with an aqueous extractant to extract the alkali metal halides from the organic phase into an aqueous extractant phase, and separating the aqueous extractant phase from the organic phase solution; titrating the alkali metal halides in the aqueous extractant phase with a premeasured quantity of a titrant; and then contacting the titrated aqueous extractant phase with an indicator which acquires a characteristic color depending upon whether or not the quantity of alkali metal halides present in the aqueous extractant phase is sufficient to react with all of the added titrant, whereby the resultant color provides the detectable indication of whether or not a pre-selected level of halogen was present in the soil sample.

11. The method of claim 10 wherein the titrant is mercuric nitrate and the halogen is selected from the group consisting of chlorine, bromine and iodine.

12. The method of claim 10 wherein the titrant is mercuric nitrate and the halogen is chlorine.

13. The method of claim 1 including carrying out step (b) by shaking a container containing the soil sample and the water, and carrying out step (c) by shaking a container containing the soil sample and the organic solvent.

14. The method of claim 2 including carrying out steps (b) and (c) simultaneously by shaking a container containing the soil sample and the mixture of water and the organic solvent.

15. The method of claim 1, claim 2 or claim 3 wherein the halogenated organic compound is a halogenated hydrocarbon.

16. The method of claim 1, claim 2 or claim 3 wherein the halogenated organic compound is PCB.

* * * * *

UNITED STATES PATENT AND TRADEMARK OFFICE
CERTIFICATE OF CORRECTION

PATENT NO. : 5,028,543

DATED : July 2, 1991

INVENTOR(S) : Stephen R. Finch and David J. Fischer

It is certified that error appears in the above-identified patent and that said Letters Patent is hereby corrected as shown below:

```
In column 2, line 34, "shileds" should read --shields--, and in
              line 35, "water immiscible" should be hyphenated.
In column 6, line 67, "facilatate" should read --facilitate--.
In column 9, line 30, "concentrations" should read --concentra-
    tion--.
In column 10, line 11, "titant" should read --titrant--, and in
               line 47, "whether of not" should read --whether
                        or not--.
Col. 11, line 4, the heading on the left side of the table should
    read --Corresponding Item--.
In column 12, line 56, "quanitative" should read --quantitative--.
In claim 10, column 14, line 22, "premeasured" should be
    hyphenated, and in
                line 29, "whether of not" should read
                         --whether or not--.
```

Signed and Sealed this

Second Day of March, 1993

*Attest:*

STEPHEN G. KUNIN

*Attesting Officer*  Acting Commissioner of Patents and Trademarks